US012570587B2

(12) United States Patent
Gosangari et al.

(10) Patent No.: US 12,570,587 B2
(45) Date of Patent: Mar. 10, 2026

(54) HIGH TEMPERATURE FINAL DEHYDRATION REACTOR IN DEHYDRATION PROCESS TO PREVENT DIETHYL ETHER PRODUCTION

(71) Applicant: UOP LLC, Des Plaine, IL (US)

(72) Inventors: Saikrishna Laxmirajam Gosangari, Gurugram (IN); Manuela Serban, Northbrook, IL (US); Ashish Mathur, Gurgaon (IN); Balkrishna Tope, Gurgaon (IN)

(73) Assignee: UOP LLC, Rosemont, IL (US)

( * ) Notice: Subject to any disclaimer, the term of this patent is extended or adjusted under 35 U.S.C. 154(b) by 0 days.

(21) Appl. No.: 18/457,259

(22) Filed: Aug. 28, 2023

(65) Prior Publication Data

US 2024/0067585 A1     Feb. 29, 2024

(30) Foreign Application Priority Data

Aug. 30, 2022    (IN) .............................. 202211049529

(51) Int. Cl.
*C07C 1/24* (2006.01)
(52) U.S. Cl.
CPC ............ *C07C 1/24* (2013.01); *C07C 2521/04* (2013.01)

(58) Field of Classification Search
CPC .............. C07C 1/24; B01J 8/0469; B01J 8/06
See application file for complete search history.

(56) References Cited

U.S. PATENT DOCUMENTS

2010/0145125 A1    6/2010  Xie et al.
2015/0265992 A1*   9/2015  Taheri ...................... B01J 8/025
                                                422/652

FOREIGN PATENT DOCUMENTS

CN          101244970 A    8/2008
CN          113045372 A    6/2021
EP           2108635 A1   10/2009

OTHER PUBLICATIONS

Search Report and Written Opinion for PCT/US2023/073161 dated Dec. 18, 2024.

* cited by examiner

*Primary Examiner* — Sharon Pregler
(74) *Attorney, Agent, or Firm* — Paschall & Associates, LLC; Mark Goldberg

(57) ABSTRACT

A process of converting an ethanol feed stream to ethylene comprising sending portions of said ethanol feed stream to two reactors in parallel and then sending the combined product to a third reactor that is operated at a higher temperature to prevent the formation of ethers such as diethyl ether.

10 Claims, 1 Drawing Sheet

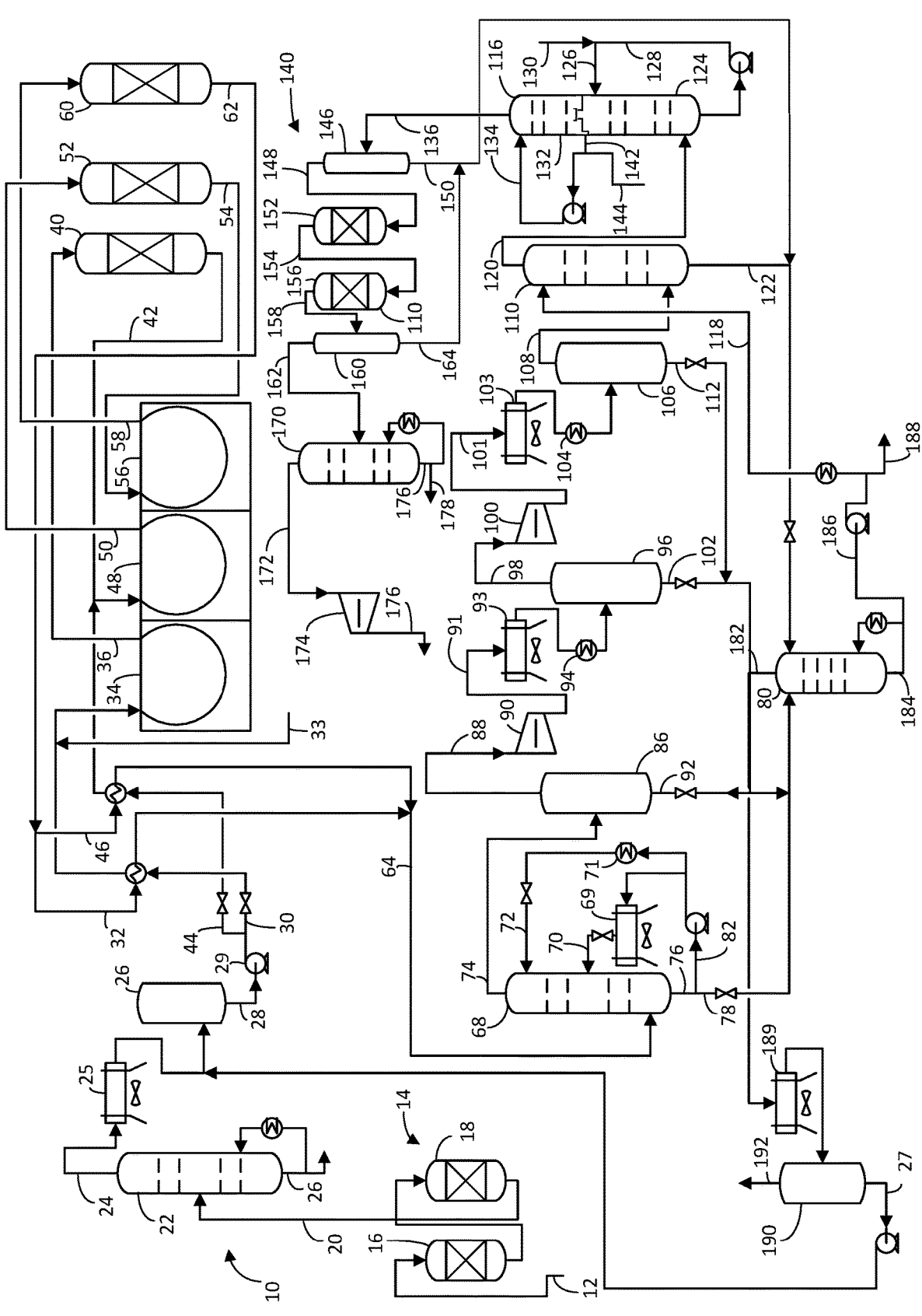

HIGH TEMPERATURE FINAL DEHYDRATION REACTOR IN DEHYDRATION PROCESS TO PREVENT DIETHYL ETHER PRODUCTION

FIELD

This application claims priority to Indian provisional patent application 202211049529 filed on Aug. 30, 2022.

The field is the conversion of alcohols to olefins. The field may particularly relate to the dehydration of ethanol to produce ethylene and the subsequent conversion of the ethylene to long chain olefins and the hydrogenation of the long chain olefins to produce paraffins and more particularly to the use of a high temperature final dehydration reactor to prevent diethyl ether production.

BACKGROUND

Oil and gas refiners worldwide are exploring methodologies and routes to reduce the carbon footprint and are moving towards sustainable processes. An ethanol to jet fuel process is one of the routes that holds promise to minimize or eliminate the customer's carbon footprint. The end product of this process is jet and diesel fuel produced out of bio ethanol. The jet fuel is a sustainable aviation fuel and is intended to replace jet fuel produced out of conventional sources such as crude oil.

There are generally three main steps in the process to convert ethanol to jet fuel. The first is to dehydrate ethanol to produce ethylene. Next the ethylene is converted to long chain olefins and then the long chain olefins are hydrogenated to generate paraffins. This disclosure is mostly concerning the conversion of an ethanol feed stream to ethylene and a significant reduction in the production of diethyl ether impurities.

BRIEF DESCRIPTION OF THE DRAWINGS

FIG. 1 is a schematic process flow diagram of the present disclosure.

SUMMARY

A process is provided of converting an ethanol feed stream to ethylene comprising dividing said ethanol feed stream into a first portion and a second portion;

sending said first portion to a reactor through a charge heater; mixing steam with said first portion at said charge heater and sending an ethanol/steam mixture to said reactor;

subjecting said ethanol/steam mixture to sufficient conditions to dehydrate said ethanol to produce an effluent comprising ethylene and water; combining said effluent with said second portion to form an effluent/second portion mixture and sending said mixture to a second reactor to be reacted to produce a product effluent comprising ethylene and water and sending product effluents from said first reactor and said second reactor to a third reactor wherein the inlet temperature for said third reactor is about 400-500° C.

Definitions

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without passing through a fractionation or conversion unit to undergo a compositional change due to physical fractionation or chemical conversion.

The term "indirect communication" means that flow from the upstream component enters the downstream component after passing through a fractionation or conversion unit to undergo a compositional change due to physical fractionation or chemical conversion.

The term "bypass" means that the object is out of downstream communication with a bypassing subject at least to the extent of bypassing.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

As used herein, the term "predominant" or "predominate" means greater than 50%, suitably greater than 75% and preferably greater than 90%.

As used herein, the term "$C_x$" are to be understood to refer to molecules having the number of carbon atoms represented by the subscript "x". Similarly, the term "$C_x-$" refers to molecules that contain less than or equal to x and preferably x and less carbon atoms. The term "$C_x+$" refers to molecules with more than or equal to x and preferably x and more carbon atoms.

As used herein, the term "carbon number" refers to the number of carbon atoms per hydrocarbon molecule and typically a paraffin molecule.

DETAILED DESCRIPTION

The ethanol dehydration process unit is divided into six main sections, the feed pretreatment section, feed purification section, reactor section, ethylene compression section and water wash section.

In the feed pretreatment section, metals may be removed by using ion-exchange resin guard beds. It is configured in lead/lag flow scheme such that one vessel can be taken offline and reloaded while one vessel is online. The ion-exchange resin vendors recommend a regenerable system using HCl or sulfuric acid as a regenerant. An HCl regenerant is not appropriate as the unit has stainless steel metallurgy. A regenerable system with sulfuric acid would need to be fully vetted and reviewed if it is to be implemented. Ion-exchange resin would have the highest capacity. Presently it is not considered necessary to have feed pretreatment for metal content below <1.0 wppm.

The demetallized product out of the feed pretreatment section is routed to the feed purification column (FPC) through the tube side of the fresh feed-overhead vapor exchanger. This column is designed to purge out the heavier molecules coming along with the ethanol feed through the column bottoms. The heavier molecules may consist of but are not limited to components such as C3+ alcohols, acetal, hexadecanoic acid, octadecanoic acid, isopentyl acetate, cyclohexanol, cyclopentanol, phenol, cresol, acetal etc. Some of these heavier molecules may convert to ketones within the reactors and tend to accumulate without exiting the process and hence need to be removed or minimized before a feed can be sent to the reactor section. The bottoms purge is expected to be <1.0% of the total feed consisting of concentrated heavies such as acetic acid, acetal, cresol, phenol, free fatty acids such as hexadecanoic acid and octadecanoic acid, some heavy alcohols etc. and the column bottom sump can be swaged and designed to hold the heavier purge material for typical 24 hrs and purged out to the ethanol slops tank.

Since there are no dissolved light ends expected with the ethanol feed stock, a total condensing system is suitable for this column. The receiver pressure controlled by nitrogen push-pull system is set to allow for using MP steam as reboiling medium for the column. The vapor from the column overhead is first condensed on the shell side of the fresh feed-overhead vapor exchanger followed by feed purification column overhead condenser before entering the feed purification column receiver. The receiver liquid at its bubble point is pumped by the feed purification column net overhead pumps and further subcooled in the feed purification column net overhead cooler. The subcooled material is mixed with the liquid ethanol recycle stream and cooled in the DEE absorber feed cooler before entering the DEE absorber on the top tray or the feed surge drum (see discussion below).

The diethyl ether (DEE) Absorber is floating with the dehydration separator vapor stream which enters below the bottom tray of the DEE absorber and this column is provided to remove diethyl ether from the dehydration separator vapor. The DEE absorber bottom sump is designed to provide 15 mins residence time to the liquid feed entering the reactor section. If a DEE absorber is not considered as part of design, then a feed surge drum with a residence time of 15 minutes should be provided and the FPC net overhead liquid mixed with the recycle ethanol would enter the feed surge drum instead of DEE absorber. If the FPC is not included as part of design, then the fresh ethanol feed plus the recycle ethanol stream can be routed to either the DEE absorber (if considered part of the particular design) or the feed surge drum.

The reactor section includes the following elements. The feed surge drum liquid or the DEE absorber bottoms liquid stream is pumped to the reactor section via the dehydration charge pumps. The discharge stream is first preheated in the ethanol treated water exchanger. The preheated ethanol is split into two streams on flow control. The first split of feed stream is heated and vaporized in the ethanol-jet product exchanger, ethanol-hydrogenation reactor feed exchanger (both these exchangers are located in the oligomerization unit) and the first ethanol steam heater before entering the cold side (tube side) of the combined feed exchanger 1 (CFE1) followed by the charge heater. Before entering the CFE1, the vaporized feed is mixed with steam generated in the steam generators placed in the downstream oligomerization unit. The combined stream is heated to required reaction temperature in the charge heater and routed to the first reactor.

The ethanol dehydration reactions are endothermic in nature. Water is a byproduct of the dehydration reactions and the water generated in the first reactor caters to the steam requirement in the downstream reactors. The second split of feed stream is heated and vaporized in the ethanol-second stage oligomerization lag reactor feed exchanger, ethanol-second stage oligomerization lead reactor feed exchanger (both these exchangers are located in the oligomerization unit) and the second ethanol steam heater before entering the cold side (tube side) of the second combined feed exchanger (CFE2). At the cold side outlet of CFE2, the feed stream is mixed with the first reactor effluent and routed to the first interheater where the stream is further heated to required reaction temperature. Steam does not take part in the reaction (except may be some minor side reactions) but the steam added in the reactor serves the dual purpose of controlling the endotherm across the reactor as well as maintaining the stability of the catalyst (reducing coke laydown). Minimizing temperature drop across the reactor is critical because at the lower reactor outlet temperature, the formation of diethyl ether is more pronounced. To ensure that the diethyl ether formation is limited, the second reactor effluent is passed through the second Interheater and again heated up to required reactor temperature before routing to the third reactor. The third reactor is a polishing reactor which ensures that the diethyl ether along with unconverted ethanol is converted to useful ethylene. The third reactor effluent is split and passes through the hot side (shell side) of the CFE1 and CFE2. The hot side outlet from the combined feed exchangers is further cooled and condensed in the waste water stripper reboiler followed by the dehydration product condenser before entering the dehydration separator.

The dehydration separator liquid stream is mainly water with some dissolved oxygenates and the stream is routed to the low-pressure waste water stripper while the vapor stream is essentially the ethylene product. As noted above, the dehydration separator vapor is routed to the DEE absorber. If the DEE absorber is not considered as part of design, then the separator vapor is routed to the water wash tower.

The fired heaters used in the reactor section are designed as natural draft furnaces with the main process heating happening in the radiant section while the convection section of these fired heaters is designed to generate high pressure steam.

The ethylene compression section involves the following factors. The pressure requirement of the vapor product stream to the downstream oligomerization unit is in excess of 1000 psig and this is achieved by a four or five stage compressor system. Four stages may be specified with a reciprocating machine while five stages may be specified with a centrifugal machine. In one embodiment there would be four stage reciprocating machine with one operating and one standby. The number of stages may be based on the downstream unit pressure requirement as well as limiting the compressor discharge temperature to less than 90° C.

The vapor from the water wash tower mixes with the first stage ethylene compressor spillback before entering the first stage ethylene compressor suction drum to knockout any entrained liquid. The vapors from the drum are compressed in the first stage ethylene compressor and the compressor discharge is cooled in the first stage discharge cooler and the first stage discharge trim cooler, the cooled stream further mixes with the second stage ethylene compressor spillback and enters the first stage ethylene compressor discharge drum. The vapors from the first stage ethylene compressor discharge drum are split into two streams, the first stream is the first stage ethylene compressor spillback while the second stream is the net vapor stream entering the second stage ethylene compressor. The vapors are further compressed in the second stage ethylene compressor and the compressor discharge is cooled in the second stage discharge cooler and second stage discharge trim cooler; the cooled stream further mixes with the third stage ethylene compressor spillback and enters the second stage ethylene compressor discharge drum. The vapors from the second stage ethylene compressor discharge drum are split into two streams, the first stream is the second stage ethylene compressor spillback while the second stream is the net vapor stream entering the third stage ethylene compressor. The vapors are further compressed in the third stage ethylene compressor and the compressor discharge is cooled in the third stage discharge cooler and third stage discharge trim cooler before entering the third stage ethylene compressor discharge drum. The vapors from the third stage ethylene compressor discharge drum are split into two streams, the first stream is the third stage ethylene compressor spillback while the second stream is the net vapor product which enters the ethylene driers for removing saturated moisture. The dried vapors from the ethylene driers are mixed with the fourth stage ethylene compressor spillback and enter the fourth stage ethylene compressor suction drum. The vapors are compressed in the fourth stage ethylene compressor before entering the fourth stage ethylene compressor discharge drum. The fourth stage ethylene compressor discharge drum vapor is split into two streams, the first stream is the fourth stage ethylene compressor spillback while the second stream is the net vapor product which is routed to the oligomerization unit. The fourth stage ethylene compressor discharge is not cooled unlike upstream stages, and the hot vapor stream is directly routed to the oligomerization unit. To ensure that the fourth stage ethylene compressor discharge temperature does not exceed recommended limits, a fourth stage spillback cooler is added on the compressor spillback line.

The saturated moisture in the vapor from the water wash tower are partially knocked out in the first stage ethylene compressor suction and discharge drum and the second and third stage ethylene compressor discharge drums. The knocked out liquid is mostly water, and this condensation is due to increase in pressure and drop in intermediate temperature. The knockout drum liquid is routed to waste water stripper.

Two ethylene driers loaded with molecular sieves are specified for moisture removal from the ethylene vapor product, and these are operated in lead-lag mode. Once the lead drier molecular sieves are saturated with moisture, the drier needs to be regenerated to restore the sieve capacity. The dried ethylene vapors coming out of the lag drier are used as regenerant medium. A slip stream from the lag drier outlet is routed to the regenerant superheater where the regenerant is heated up to required regeneration temperature before entering the drier under regeneration. The spent regenerant carrying the desorbed moisture out of the molecular sieves from the drier under regeneration is cooled and condensed in the regenerant condenser before entering the regenerant coalescer. The regenerant coalescer separates the water from the spent regenerant i.e. ethylene and this ethylene vapor is routed back to the first stage ethylene compressor suction drum on pressure control while the spent water is routed to the waste water stripper.

The waste water section consists of the waste water stripper and the water wash tower. The liquid from the dehydration separator, water wash tower bottoms, regenerant coalescer (intermittent) as well as knocked out liquid from the ethylene compressor section knockout drums is routed through the shell side of the waste water stripper feed-bottoms exchanger before entering the top tray of the waste water stripper. The waste water stripper is designed to strip off the oxygenates coming in with the feed as an overhead vapor product while recovering treated water in the bottoms.

The waste water stripper operates at 5-10 psig and the overhead vapors are cooled and condensed in the off-gas condenser before entering the off-gas knockout drum. The off-gas knockout drum liquid has majority of the alcohols carried over from the DEE absorber vapor (if DEE absorber is part of design), unconverted alcohols from the reactor, water along with other non-selective oxygenates formed within the reactor such as acetaldehyde, ethers, acetic acid etc., which are recycled and mixed with the fresh feed and routed to the reactor section through the feed surge drum or the DEE absorber bottoms (if included as part of design). The off-gas knockout drum vapor is a small purge stream which is a mix of olefins (dissolved in the dehydration separator and water wash tower liquid) as well as oxygenates. This purge gas stream is mixed with the low pressure off gas streams generated in the downstream oligomerization Unit and further compressed in the waste off gas compressor to required fuel gas knockout drum pressure before being burned off in the complex fired heaters. The waste water stripper has two reboiler systems. One reboiler i.e. the waste water stripper auxiliary reboiler utilizes low pressure steam as reboiling medium (expected to be operated at start-up and as an auxiliary backup) while the other reboiler i.e., the waste water stripper reboiler is process heat integrated with the hot dehydration reactor effluent upstream of the dehydration product condenser. The waste water stripper net bottoms is pumped by the treated water pumps through the tube side of the waste water stripper feed-bottoms exchanger and downstream is split into three streams. The first stream is the treated water used for vapor product oxygenate wash in the water wash tower. This stream is routed to the Water wash tower via the ethanol-treated water exchanger, treated water cooler and treated water trim cooler.

The second stream is the treated water quantity corresponding to the steam injected into the dehydration reactors plus 5% blowdown. This stream is routed to the steam generators placed in the downstream oligomerization unit reactor section for heat recovery. The steam generated is recycled back to the dehydration reactor to meet the steam to ethanol ratio requirement. The continuous blowdown from steam generators is directly routed to the waste water treatment facility. This stream is split at the upstream of the ethanol-treated water exchanger.

The third stream is the net treated water generated out of the various reactions occurring in the reactor section and is routed to the waste water treatment facility and this stream is taken from downstream of the treated water trim cooler.

As noted previously, the dehydration separator vapors can be routed to the DEE absorber (if included as part of design) or the water wash tower. The dehydration separator vapors have certain impurities/oxygenates such as acetaldehyde, diethyl ether, dimethyl ether, water, unconverted alcohols etc. which need to be removed before routing the vapor product stream to the downstream oligomerization unit.

With a DEE absorber, the diethyl ether in the separator vapor is absorbed in the bottom liquid along with some other oxygenates. Since ethanol feed is used for washing the separator vapor, there is carry over of some ethanol feed to the DEE absorber vapors. The DEE absorber overhead vapors are routed below the bottom tray of the water wash tower. The water wash tower is designed to wash off oxygenates such as acetaldehyde, unconverted alcohols from the reactor section, ethanol carryover from the DEE absorber vapors, acetic acid etc. using treated water from the waste water stripper bottoms. The treated water enters the top tray of the water wash tower and the absorption of oxygenates occurs in a counter current direction over multiple trays. The water wash tower overhead vapors after the wash are routed to the downstream ethylene compression section, while the liquid bottoms stream with all the dissolved oxygenates/alcohols are routed to the waste water stripper.

The ethanol feeds are derived out of either a wet mill or dry mill process. These ethanol feeds can contain a variety of contaminants such as higher alcohols, metals, acetaldehyde, ethyl acetate, etc. In addition, the dry mill feed can also contain fusel oils (heavier alcohols and acids). The ethanol feed may be treated to remove metal contaminants through the use of resin treaters. The heavy hydrocarbon from the fresh feed can be knocked out in a feed purification column.

Presently in the ethanol dehydration process unit, the feed to the reactor section is split into two parallel reactors. This is done to minimize the steam requirement for the unit. With a lower steam level, the parallel reactor endotherms are quite high resulting in the reactor outlet temperatures in the range of 300 to 340° C. At such low outlet temperatures, the ethanol in the reactor can form the undesirable diethyl ether. Present innovation intends to mitigate diethyl ether formation which is a non-elective component and results in selectivity loss. Since the first 2 parallel reactors have a process outlet temperature in the range of 300-340° C., there is potential to form diethyl ether within the reactor mostly in the colder section of these reactors. Pilot plant data also indicates formation of the ether at lower temperatures. To ensure that the diethyl ether is not formed, a 3rd reactor (polishing reactor) along with an Interheater is added at the outlet of the parallel reactors. The 3rd reactor inlet has very less unconverted ethanol and the inlet temperature is maintained high enough in the range of 400-500 Deg C. to avoid any ether formation. Also, since the ethanol concentration at the inlet of the 3rd reactor is lower, the expected endotherm in the 3rd reactor is small and this prevents any possibility of ether formation.

A fresh ethanol feed is combined with unconverted ethanol and is split into two equal streams into parallel combined feed exchangers. A split reactor configuration is considered because a desired steam to ethanol ratio is maintained at the reactor inlet to maintain the reactor endothermicity as well as ensuring catalyst stability. In order to minimize the combined feed rate to reactor, it becomes essential that the steam intake is reduced. The ethanol dehydration reaction results in generation of water as a byproduct.

The fresh feed to the reactor section may be equally split via two combined feed exchangers. Feed from the CFE1 is routed to reactor 1 via the charge heater. Steam is mixed with the fresh feed at the charge heater inlet. Since only half the feed is routed through reactor 1, the required steam level is just half of the required steam. Water is generated out of the dehydration reaction in reactor 1 and the reactor 1 effluent is mixed with the fresh feed routed through CFE 2 and interheater No 1 into reactor No 2. The water generated in reactor No 1 caters to the steam to ethanol ratio requirement in reactor. With this innovation, the steam requirement is dropped by 50%, thereby reducing the entire reactor combined feed capacity by 30-40%. As a further additional item to the feed section, the diluted ethanol feed can also be processed within the reactor section. When more diluted ethanol feed is processed within the dehydration section, the amount of steam required is reduced. Diluting the ethanol feed has the benefit of reducing the utility consumption in the upstream ethanol production unit. Diluting the ethanol feed below 90% does not yield significant utility savings.

As already explained, water is generated as a byproduct from the ethanol dehydration reaction. A part of the water generated within the process is recycled and mixed with fresh feed routed to reactor no 1 at the CFE 1 inlet. The recycle water is split into two streams. One stream is routed via a fired heaters convection section (50-60%) to generate steam and the rest of the water is mixed with the fresh feed at CFE1 inlet. This poses a unique problem since the vaporization of liquid water along with ethanol must happen on the cold side of the CFE1. Given that the cold side is at a higher pressure and is boiling and the hot side is at a lower pressure and condensing, the available approach drops drastically making the CFE design impractical. To ensure that enough approach is available in the CFE1, either the cold side pressure needs to be dropped or the hot side pressure needs to be increased. This is achieved by including an interreactor compressor at reactor No 1 outlet. The reactor No 1 outlet is operated at a lower pressure there by reducing the CFE 1 cold side inlet pressure. The reactor 1 effluent is compressed and mixed with the fresh feed entering reactor no 2. This option presents a unique opportunity to improve the energy recovery from reactor effluent in the combined feed exchanger thereby reducing the utility in the charge heater as well as the products condenser.

A second option for the reactor section design may be considered, The interreactor compressor is a large piece of equipment and even though it helps reduce utility consumption, it is costly as well as difficult to design. One of the major reasons to have this compressor is to ensure that the recycle water is effectively vaporized. This embodiment is developed to eliminate this water recycle. Instead the steam requirement for the dehydration reactors are met with the steam generated in the downstream oligomerization/hydrogenation unit. Partially the steam can also be generated using BFW in the fired heater convection section. The reactor effluent in this option now is utilized to just vaporize the ethanol feed and an interreactor compressor is not required.

Without an interreactor compressor, the product condenser duties increase by 20-30%. However, this option presents a much easier design.

Combined Feed Exchangers—Both the combined feed exchangers are expected to be vertical exchangers.

Reactors—Given that the reactor section operates at a very low pressure, high temperature, and the gas molecular weight varies from 20-30, the volumetric rates through the reactor are very large which results in excessive bed pressure drop using conventional fixed bed downflow reactor. The pressure drop concerns can be assuaged by either designing a fixed bed radial flow design or a compartmental reactor design.

Fired Heaters—The fired heaters are expected to be box type furnaces with process heating in the radiant section. The convection section can be utilized to generate steam which can be used in the dehydration process.

The reactor effluent out of the CFE can be either routed to a separator via the products condenser/products trim condenser or can be routed through a quench tower. The separator design is a conventional design and is not deliberated further.

The quench tower is a unique design where in the hot effluent from the CFEs is routed below the bottom tray. The liquid effluent is separated and the hot vapor effluent is recontacted with recycle water. The heat within the reactor effluent is absorbed by the recycling water stream which is cooled in a product condenser/trim condenser. The cooled vapor out of the quench tower/separator is compressed in a two stage compressor. There are intermediate coolers/trim coolers to maintain the process gas temperature. The ethylene rich vapor out of the compressor is routed to the water wash tower for oxygenate removal.

The net waste water from the quench tower bottoms/separator bottoms has unconverted ethanol and other dissolved oxygenates. This stream is routed to a waste water stripper. A waste water stripper is steam reboiled to recover dissolved oxygenates and unconverted ethanol as a vapor product. The vapor from the waste water stripper is condensed and routed to a knockout pot for unconverted ethanol recovery. This unconverted ethanol along with some other dissolved oxygenates are pumped back to the reactor section for further conversion.

The waste water stripper bottoms is now 99.9 mol % pure water and may be used as a washing medium to scrub the oxygenates out of the ethylene vapor stream coming from the second stage ethylene compressor in the water wash tower. Apart from using the waste water stripper bottoms as a washing medium in the water wash tower, a net water draw is also taken out from the process. This water can be used in an electrolyzer unit for green hydrogen generation or can be routed to further treatment for ppm level oxygenate removal before being used for steam generation. The waste water stripper bottoms stream is routed to the top tray of the water wash tower while the vapor from the second stage compressor discharge is routed below the bottom tray of the water wash tower. The intent is to wash the ethylene rich vapor stream and remove the oxygenates as much as possible from the product stream. Some of the oxygenates are not effectively removed such as ethers (dimethyl ether and diethyl ether), carbon dioxide and carbon monoxide. The carbon dioxide can be removed in a two-stage caustic scrubbing process while the oxygenates can be further removed in a cryogenic distillation unit.

The vapor from the above treatment is further passed through a set of driers to remove the moisture in the vapor stream and routed to the cryogenic distillation unit. The vapor from the cryogenic distillation unit is further compressed in a third stage of ethylene compressor to meet the downstream unit battery limit pressure requirement In FIG. 1, in accordance with an exemplary embodiment, a process 10 is shown for processing an oxygenate feedstock. The oxygenate feedstock may comprise alcohol and preferably comprises ethanol. The feedstock may comprise a predominance of ethanol and may be aqueous. Preferably, the oxygenate feedstock is a biorenewable feedstock.

A feed line 12 transports an oxygenate stream of oxygenate feedstock to a feed pretreatment section 14. The feed pretreatment section 14 comprises a vessel 16 comprising a bed of cationic exchange resin adsorbent for removing metal contaminants, such as sodium, zinc, phosphates, copper, and calcium from the oxygenate stream in the feed line 12. The feed pretreatment section 14 may comprise an additional vessel 18 with a bed of the same adsorbent for further removing metals from the oxygenate stream. The vessels 16, 18 may be in series or in a lead-lag type of arrangement to allow for regeneration of spent adsorbent. Line 17 transports partially pretreated oxygenate stream from an outlet of vessel 16 to the inlet of vessel 18. A pretreated oxygenate stream exits the feed pretreatment section 14 in line 20 from an outlet of the additional vessel 18 and is fed to a purification column 22. The feed pretreatment section 14 may be operated at a temperature of about 32° C. to about 104° F. and a pressure of about atmospheric pressure to about 670 kPa(g) psig).

In the purification column 22, the pretreated oxygenate stream is fractionated to separate ethanol from heavier oxygenates also known as fusel oil such as cyclohexanol, cyclopentanol, and heavier alcohols and acids. The purification column 22 is operated to minimize ethanol to no more than 1% of feed in bottom stream in line 26. A heavy oxygenate stream in a bottoms line 26 is taken from a bottom of the purification column 22 to heavy oxygenate treatment. The purification column 22 may be reboiled by heat exchange with a suitable hot stream such as steam to provide the necessary heat for the distillation. The purification column 22 provides an overhead gaseous stream of purified ethanol in an overhead line 24 which may be cooled in an air cooler 25 and fed to a feed surge drum 26 along with a recycle ethanol stream in line 27. The purification column 22 may be operated with a bottoms temperature between about 82° C. and about 121° C. and an overhead pressure of about 35 kPa (g) to about 140 kPa (g).

Ethanol in the feed surge drum 26 may be blanketed with nitrogen. A charge pump 29 pumps an ethanol charge stream in line 28 into two charge streams. A first charge stream in line 30 is heat exchanged with a first dehydrated exchange stream in line 32, mixed with steam in line 33 and fed to a first charge heater 34. The first charge heater 34 may be a fired heater and may heat the first charge stream to about 400° C. to about 550° C. A resulting first heated charge stream in line 36 is charged to a first dehydration reactor 40. In the first dehydration reactor 40, ethanol feed is converted to ethylene and water over a dehydration catalyst at a pressure of about 455 kPa (g) to about 630 kPa (g). A first dehydrated stream is discharged from the first dehydration reactor 40 in line 42.

A second charge stream in line 44 is heat exchanged with a second dehydrated exchange stream in line 46, mixed with the first dehydrated stream in line 42 and fed to a second charge heater 48. The second charge heater 48 may be a fired heater and may heat the second charge stream to about 400° C. to about 550° C. A resulting second heated charge stream in line 50 is charged to a second dehydration reactor 52. In the second dehydration reactor 52, ethanol feed is converted to ethylene and water over a dehydration catalyst at a pressure of about 420 kPa (g) to about 700 kPa (g). A second dehydrated stream is discharged from the second dehydration reactor 52 in line 54.

The second dehydrated stream in line 54 is fed to an interheater 56. The interheater 56 may be a fired heater and may heat the second dehydrated stream to about 400° C. to about 550° C. A resulting third heated charge stream in line 58 is charged to a third dehydration reactor 60. In the third dehydration reactor 60, residual ethanol feed is converted to ethylene and water over a dehydration catalyst at a pressure of about 420 kPa (g) to about 700 kPa (g). A third dehydrated stream is discharged from the third dehydration reactor 60 in line 62.

The dehydration catalyst is an alumina-based catalyst.

The third dehydrated stream is split between the first dehydrated exchange stream in line 32 and the second dehydrated exchange stream in line 46. The first dehydrated exchange stream in line 32 is heat exchanged with the first charge stream in line 30, and the second dehydrated exchange stream in line 46 is heat exchanged with the second charge stream in line 44 and the cooled dehydrated streams are recombined in line 64.

The cooled dehydrated stream in line 64 is fed to a quench tower 68 in which the cooled dehydrated stream is quenched by direct contact with water from a first cooled water stream in line 70 and a second cooled water stream in line 72. A quenched ethylene stream exits in a quench overhead line 74 and a bottoms water stream exits the tower bottoms in line 76. The bottoms water stream is split between a drain stream in line 78 which may be transported to a waste water stripper column 80 through a control valve thereon and a quench recycle stream in line 82. A first portion of the quench recycle stream is air cooled in a product condenser 69 and recycled as the first, lower cooled water stream in line 70 through a control valve thereon, and a second portion of the quench recycle stream is heat exchanged in a trim condenser 71 and recycled to the quench tower 68 as the second, higher cooled water stream in line 72. The quench tower 68 may be operated with a bottoms temperature of about 37° C. to about 104° C. and a pressure of about 280 kPa (g) to about 490 kPa (g) in the overhead.

The quenched ethylene stream in line 74 is fed to a first stage suction drum 86. In the first stage suction drum ethylene exits the overhead line 88 to a first stage compressor 90 while residual water exits the bottom of the drum in line 92 through a control valve thereon and is transported to the waste water stripper column 80 perhaps via line 78. The first stage compressor 90 compresses the ethylene stream to a first pressure of about 350 kPa (g) to about 1225 kPa (g) and the discharge in line 91 is cooled in a first stage discharge cooler 93 and a first stage trim cooler 94.

The cooled, compressed ethylene stream from the first stage trim cooler 94 is fed to a first stage discharge drum 96. From the first stage discharge drum 96 ethylene exits in an overhead line 98 to a second stage compressor 100 while residual water exits a bottom of the drum in line 102 through a control valve thereon and is transported to the waste water stripper column 80 perhaps via lines 92 and 78. The second stage compressor compresses the ethylene stream to a second pressure of about 455 kPa (g) to about 3220 kPa (g) and the discharge in line 101 is cooled in a second stage discharge cooler 103 and a second stage trim cooler 104.

The twice cooled, compressed ethylene stream from the second stage trim cooler 104 is fed to a second stage discharge drum 106. From the second stage discharge drum

106 ethylene exits in an overhead line 108 and is transported to a water wash tower 110 while a residual water stream exits the bottom of the drum in line 112 through a control valve thereon and is transported to the waste water stripper column 80 perhaps via lines 102, 92 and 78.

In the water wash tower 110, the twice cooled, compressed ethylene stream is counter-currently washed with cooled, treated water in line 118 from the waste water stripper column 80 to absorb additional oxygenates to produce a washed ethylene stream exiting in an overhead line 120 and a wash water stream in a bottoms line 122. The washed ethylene stream in the overhead line 120 is transported to a caustic scrubber column 116. The wash water stream in line 122 is transported back to the water stripper column 80 through a control valve thereon. The wash water 110 may be operated with a bottoms temperature of about 16° C. to about 82° C. and a pressure of about 2800 kPa (g) to about 3500 kPa (g) in the overhead.

The caustic scrubber column 116 has a lower caustic wash section 124 and an upper water wash section 132. In the lower caustic wash section 124 the washed ethylene stream in line 120 is scrubbed with an aqueous caustic stream from line 126 to absorb acid gases such as carbon dioxide from the washed ethylene stream. Spent caustic is pumped around from the bottom of the lower section in line 128 and replenished with fresh caustic in line 130 to provide the aqueous caustic stream 126. A scrubbed vaporous ethylene stream depleted of acid gases ascends from the caustic wash section 124 to the upper water wash section 132 through a vapor inlet. In the water wash section 132, the scrubbed ethylene stream is contacted with a wash water stream from line 134. A washed, scrubbed vaporous ethylene stream exits the overhead of the water wash section 132 in line 136 and is fed to the product drier section 140. A spent water stream is taken from the bottom of the water wash section 132 from a liquid sump in line 142 and replenished with a fresh water stream from line 144 to provide the wash water stream in line 134 and pumped to the top of the water wash section 124 to be contacted with the scrubbed vaporous ethylene stream. The caustic scrubber column may be operated with a bottoms temperature of about 38° C. to about 43° C. and a pressure of about 2800 kPa (gauge) to about 2975 kPa (g) in the overhead.

In the product drier section 140, the washed, scrubbed ethylene stream in line 136 is fed to a first drier inlet knock-out drum 146 to remove residual water and provide a drier inlet stream in line 148 and a knock-out water stream in the bottoms line 150 which is fed to the waste water stripper column 80 perhaps via line 122. The drier inlet stream is fed to a first product drier 152 in line 148. The first product drier 152 comprises an adsorbent for adsorbing the water from ethylene in the drier inlet stream in line 148 to provide a dried ethylene stream. The adsorbent may be a molecular sieve material with pore diameters of 2-4 A. The first product drier 152 may operate in upflow mode. The product drier section 140 may include a second product drier 156 that operates as the first product drier 142. The two product driers may be operated in series but are preferably arranged in a lead-lag operation to facilitate regeneration during continuous operation. The second product drier 156 comprises an adsorbent for adsorbing the water from ethylene like in the first product drier 152. A dried ethylene stream exits the product drier section 140 in a dried ethylene stream in line 158. The product drier section 140 may be operated at a temperature of about 32° C. to about 49° C. and a pressure of about 2758 kPa(g) to about 3310 kPa(g).

The dried ethylene stream in line 158 is fed to a drier outlet knock-out drum 160 to remove residual water and provide a drier outlet stream in line 162 and a second knock-out water stream in a bottoms line 164 which is fed to the waste water stripper column 80 perhaps via lines 150 and 122.

The drier outlet stream in line 162 may be fed to a heavy oxygenates removal column 170 to separate an overhead stream comprising predominantly ethylene but perhaps higher olefins from heavy ketones and diethyl ether. The olefins are produced in an overhead line 172 and fed to a third stage compressor 174 and a bottoms heavy oxygenate stream is produced in a bottoms line 176. A heavy oxygenate purge stream may be taken in line 178 to heavy oxygenate treatment while a reboil portion is reboiled and fed back to the column 170. A compressed ethylene stream at a pressure of about 2800 kPa (g) to about 7000 kPa (g) in a compressor discharge line 176 may be provided to a dimerization section. The heavy oxygenate removal column 170 may be operated with a bottoms temperature of about −29° C.) to about (121° C.) and a pressure of about 2410 kPa(g) to about 2380 kPa(g) in the overhead.

Water streams comprising oxygenates and volatiles in lines 92, 102, 112, 122, 150, 164 may be fed to the waste water stripper column 80 in which volatiles and oxygenates are boiled off to provide an overhead volatile stream in line 182 and a stripped water stream in line 184. A portion of the stripped water stream can be reboiled and fed back to the column to provide necessary heat. A treated water stream in line 186 may be pumped to water outlets in line 188 which includes the cooled, treated water stream in line 118 for the water wash tower 110. The waste water stripper column 80 may be operated with a bottoms temperature of about 93° C. to about (121° C.) and a pressure of about 34 kPa(g) to about 138 kPa(g) in the overhead.

The overhead volatile stream in line 182 may be cooled in an air cooler 189 and fed to an off-gas knock out drum 190. An overhead stream from the knock out drum 190 in line 192 may be sent to flare while an ethanol recycle stream is pumped to the feed surge drum 26 in line 27 perhaps via line 24.

In a comparison of a two reactor system and a three reactor system in a split reactor configuration, since the overall steam injection has been reduced, the second reactor's effluent temperature is lower as compared to a series reactor configuration. At lower reactor temperatures, the diethyl ether formation is more pronounced as seen in the following table:

TABLE 1

| | Units | Split 2 reactors | Series 2 reactors |
|---|---|---|---|
| Feed Rate | Lb/Hr | 230530 | 230530 |
| Oxygenates in vapor product | MOLPPM | 151.9 | 35.1 |
| Diethyl ether in vapor product | MOLPPM | 137.8 | 1.3 |
| Reactor 1 inlet temperature | DEG F. | 842 | 842 |
| Reactor 1 Outlet temperature | DEG F. | 528 | 526 |
| Reactor 1 endotherm | DEG F. | 314 | 316 |
| Reactor 2 inlet temperature | DEG F. | 842 | 842 |
| Reactor 2 outlet temperature | DEG F. | 592 | 835 |
| Reactor 2 Endotherm | DEG F. | 250 | 7.0 |

To eliminate concern of diethyl ether formation, a second interheater and a third reactor was added. Without the third reactor, the expected diethyl ether in the vapor product is 130-150 mol ppm while this drops to less than 5 mol ppm with a third reactor as seen in Table 2.

TABLE 2

| | Units | Split 2 reactors | Split 3 reactors |
|---|---|---|---|
| Feed Rate | Lb/Hr | 230530 | 230530 |
| Oxygenates in vapor product | MOLPPM | 151.9 | 15.4 |
| Diethyl ether in vapor product | MOLPPM | 137.8 | 1.7 |
| Reactor 1 inlet temperature | DEG F. | 842 | 842 |
| Reactor 1 Outlet temperature | DEG F. | 528 | 527 |
| Reactor 1 endotherm | DEG F. | 314 | 315 |
| Reactor 2 inlet temperature | DEG F. | 842 | 842 |
| Reactor 2 outlet temperature | DEG F. | 592 | 587 |
| Reactor 2 Endotherm | DEG F. | 250 | 255 |
| Reactor 3 inlet temperature | DEG F. | NA | 842 |
| Reactor 3 outlet temperature | DEG F. | NA | 837 |
| Reactor 3 Endotherm | DEG F. | NA | 5 |

Since the last reactor inlet only has the unconverted ethanol, ethylene and water coming in from reactor 2, more detailed testing was performed to review if there is sufficient diethyl ether conversion in the third reactor at steam to ethanol ratio of 65:1. The process conditions included catalyst amount of 19 g (about 40 cc), 75% diluted ethanol plus water plus diethyl ether (300 cc/hr), The results of using a high temperature third reactor are shown in Table 3 in which 98% ethylene selectivity was observed, diethyl ether was fully converted, some increase in acetaldehyde, butanone and acetic acid formation was observed. There was no formation of butene.

The invention claimed is:

1. A process of converting an ethanol feed stream to ethylene comprising
   a. dividing all of said ethanol feed stream into a first portion and a second portion;
   b. sending said first portion to a reactor through a charge heater;
   c. mixing steam with said first portion at said charge heater and sending an ethanol and steam mixture to said reactor;
   d. subjecting said ethanol and steam mixture to sufficient conditions to dehydrate said ethanol to produce an effluent comprising ethylene and water;
   e. combining said effluent with said second portion to form an effluent and second portion mixture and sending said mixture to a second reactor to be reacted to produce a product effluent comprising ethylene and water and sending product effluents from said first reactor and said second reactor to a third reactor wherein the inlet temperature for said third reactor is about 400-500° C.

2. The process of claim 1 wherein selectivity to ethylene is about 98%.

3. The process of claim 1 wherein selectivity to ethylene is about 98-99%.

4. The process of claim 1 wherein about 0.00% butene is produced.

5. The process of claim 1 wherein a ratio of ethanol to steam is from 1:30 to 1:100.

6. The process of claim 1 wherein a ratio of ethanol to steam is from 1:50-1:75.

7. The process of claim 1 wherein a ratio of ethanol to steam is about 1:66.

8. The process of claim 1 wherein said inlet temperature is from about 440-460° C.

9. The process of claim 1 wherein said inlet temperature is from about 450-454° C.

10. The process of claim 1 wherein a product effluent from said third reactor contains less than 5 mol ppm diethyl ether.

\* \* \* \* \*